(12) United States Patent
Sasaki et al.

(10) Patent No.: US 9,610,228 B2
(45) Date of Patent: Apr. 4, 2017

(54) TERPOLYMER-COATED POLYMER ENCAPSULATED ACTIVE MATERIAL

(71) Applicant: International Flavors & Fragrances Inc., New York, NY (US)

(72) Inventors: Takashi Sasaki, Matawan, NJ (US); Johan Pluyter, Middletown, NJ (US); Lewis Michael Popplewell, Morganville, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 263 days.

(21) Appl. No.: 14/051,815

(22) Filed: Oct. 11, 2013

(65) Prior Publication Data

US 2015/0105307 A1   Apr. 16, 2015

(51) Int. Cl.
*A61K 8/11*   (2006.01)
*C11D 3/37*   (2006.01)
*C11D 3/50*   (2006.01)
*A61Q 5/02*   (2006.01)
*A61Q 19/10*   (2006.01)

(52) U.S. Cl.
CPC ............... *A61K 8/11* (2013.01); *A61Q 5/02* (2013.01); *A61Q 19/10* (2013.01); *C11D 3/3773* (2013.01); *C11D 3/505* (2013.01)

(58) Field of Classification Search
None
See application file for complete search history.

(56) References Cited

U.S. PATENT DOCUMENTS

| | | | |
|---|---|---|---|
| 4,081,384 A | 3/1978 | Pracht | 510/523 |
| 4,234,627 A | 11/1980 | Schilling | 8/137 |
| 5,112,688 A | 5/1992 | Michael | 428/402.2 |
| 5,145,842 A | 9/1992 | Driedger et al. | 514/63 |
| 6,194,375 B1 | 2/2001 | Ness et al. | 512/4 |
| 6,248,703 B1 | 6/2001 | Finucane et al. | 510/152 |
| 6,329,057 B1 | 12/2001 | Dungworth et al. | 428/403 |
| 2004/0071746 A1 | 4/2004 | Popplewell et al. | |
| 2004/0142828 A1 | 7/2004 | Popplewell et al. | |
| 2006/0287205 A1 | 12/2006 | Popplewell et al. | |
| 2007/0123442 A1 | 5/2007 | Holzner et al. | |
| 2012/0148644 A1 | 6/2012 | Popplewell et al. | |
| 2012/0276210 A1 | 11/2012 | Dihora et al. | |
| 2014/0161759 A1* | 6/2014 | Meralli | A61K 8/4933 424/78.02 |
| 2015/0252312 A1* | 9/2015 | de Villeneuve et al. | C11D 17/009 |

FOREIGN PATENT DOCUMENTS

| | | |
|---|---|---|
| EP | 1407754 A1 | 4/2004 |
| EP | 1637188 A1 | 3/2006 |
| WO | 2012138696 A2 | 10/2012 |
| WO | 2012175677 A2 | 12/2012 |

OTHER PUBLICATIONS

Merquat™ 2001 Polymer; Products Specifications, Publication Data: Lubrizol, URL: https://www.lubrizol.com/Personal-Care/Documents/Technical-Data-Sheets/TDS-814-Merquat%E2%84%A2-2001-Polymer.pdf, (accessed on May 20, 2015).
Merquat 2003PR Polymer; Product Specifications, Publication Data: Lubrizol, URL: https://www.lubrizol.com/Personal-Care/Documents/Specifications/Merquat%E2%84%A2-2003PR-Polymer.pdf, (accessed on May 20, 2015).
Extended European Search Report for EP 14188377.7 issued on Mar. 6, 2015.

* cited by examiner

*Primary Examiner* — Necholus Ogden, Jr.
(74) *Attorney, Agent, or Firm* — Martin Zhang; XuFan Tseng; Elizabeth M. Stover

(57) ABSTRACT

A polymeric encapsulated fragrance is disclosed which is suitable for use in personal care and cleaning products. In a preferred embodiment of the invention the fragrance is encapsulated by a first polymer material to form a fragrance encapsulated polymer, the polymer encapsulated shell is then coated with a cationic polymer, preferably a terpolymer composed of methacrylamidopropyl trimethyl ammonium chloride, acrylamide and acrylic acid.

9 Claims, 1 Drawing Sheet

TERPOLYMER-COATED POLYMER ENCAPSULATED ACTIVE MATERIAL

BACKGROUND

Fragrance chemicals are used in numerous products to enhance the consumer's enjoyment of a product. Fragrance chemicals are added to consumer products such as laundry detergents, fabric softeners, soaps, detergents, personal care products, such as shampoos, body washes, deodorants and the like, as well as numerous other products.

In order to enhance the effectiveness of the fragrance materials for the user, various technologies have been employed to enhance the delivery of the fragrance materials at the desired time. One widely used technology is encapsulation of the fragrance material in a protective coating. Frequently the protective coating is a polymeric material. The polymeric material is used to protect the fragrance material from evaporation, reaction, oxidation or otherwise dissipating prior to use.

For example, U.S. Pat. No. 4,081,384 discloses a softener or anti-stat core coated by a polycondensate suitable for use in a fabric conditioner. U.S. Pat. No. 5,112,688 discloses selected fragrance materials having the proper volatility to be coated by coacervation with micro particles in a wall that can be activated for use in fabric conditioning. U.S. Pat. No. 5,145,842 discloses a solid core of a fatty alcohol, ester, or other solid plus a fragrance coated by an aminoplast shell. U.S. Pat. No. 6,248,703 discloses various agents including fragrance in an aminoplast shell that is included in an extruded bar soap.

While encapsulation of fragrance in a polymeric shell can help prevent fragrance degradation and loss, it is often not sufficient to significantly improve fragrance performance in consumer products. Therefore, methods of aiding the deposition of encapsulated fragrances have been disclosed. U.S. Pat. No. 4,234,627 discloses a liquid fragrance coated with an aminoplast shell further coated by a water insoluble meltable cationic coating in order to improve the deposition of capsules from fabric conditioners. U.S. Pat. No. 6,194,375 discloses the use of hydrolyzed polyvinyl alcohol to aid deposition of fragrance-polymer particles from wash products. U.S. Pat. No. 6,329,057 discloses use of materials having free hydroxy groups or pendant cationic groups to aid in the deposition of fragranced solid particles from consumer products.

Despite these and many other disclosures there is an ongoing need for the improved delivery of fragrance materials for various rinse-off products that provide improved performance.

SUMMARY OF THE INVENTION

The present invention is directed to a composition composed of an active material encapsulated by a polymer to create a polymer encapsulated active material, wherein the polymer encapsulated active material is further coated by a terpolymer composed of methacrylamidopropyl trimethyl ammonium chloride, acrylamide and acrylic acid. In certain embodiments, the terpolymer is combined with an anionic, nonionic or cationic polymer and/or a nonionic, cationic, amphoteric or anionic surfactant. A personal care (e.g., hair shampoo, hair rinse, bar soap, or body wash), fabric care of cleaning product containing the composition is also provides as is a method for imparting an olfactory effective amount of fragrance into a wash-off product by providing a coated polymer encapsulated fragrance to a wash-off product.

DETAILED DESCRIPTION OF THE INVENTION

Figure 1:
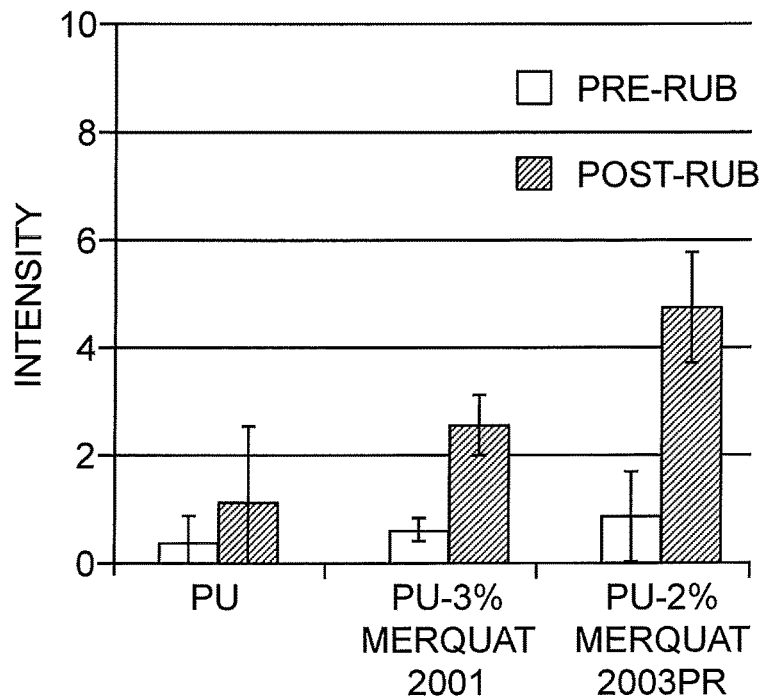
FIG. 1 shows the sensory performance of polyurea (PU) capsules of the invention in a hair shampoo formulation. Data are the averages from two separate experiments.

The present invention is directed to a polymer encapsulated active material, the polymer encapsulated active material being further treated with a polymer composed of methacrylamidopropyl trimethyl ammonium chloride, acrylamide and acrylic acid to improve deposition.

Polymer Encapsulation Systems. Encapsulation of active material such as fragrances is known in the art, see for example U.S. Pat. Nos. 2,800,457, 3,870,542, 3,516,941, 3,415,758, 3,041,288, 5,112,688, 6,329,057, and 6,261,483. Preferred encapsulating polymers include those formed from acrylates, acrylamide, acrylate-co-acrylamide, melamine-formaldehyde or urea-formaldehyde condensates, as well as similar types of aminoplasts. Other wall forming materials include polyurethane, polysiloxanes, polyurea, polyamide, polyimide, polyvinyl alcohol, polyanhydride, polyolefin, polysulfone, polysaccharide, protein, polylactide (PLA), polyglycolide (PGA), polyorthoester, polyphosphazene, silicone, lipid, modified cellulose, gums, polystyrene, and polyesters or combinations of these materials. Other polymeric materials that are functional are ethylene maleic anhydride copolymer, styrene maleic anhydride copolymer, ethylene vinyl acetate copolymer, and lactide glycolide copolymer. Biopolymers that are derived from alginate, chitosan, collagen, dextran, gelatin, and starch can also be used as the encapsulating materials. Additionally, microcapsules can be made via the simple or complex coacervation of gelatin.

Aminoplasts. A representative process used for aminoplast encapsulation is disclosed in U.S. Pat. No. 3,516,941, though it is recognized that many variations with regard to material and process steps are possible. A representative process used for gelatin encapsulation is disclosed in U.S. Pat. No. 2,800,457, though it is recognized that many variations with regard to material and process steps are possible. Both of these processes are discussed in the context of fragrance encapsulation for use in consumer products in U.S. Pat. Nos. 4,145,184 and 5,112,688 respectively. Polymer systems are well-known in the art and non-limiting examples of these include aminoplast capsules and encapsulated particles as disclosed in GB GB2006709 A; the production of micro-capsules having walls comprising styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amidoaldehyde resin in-situ polymerized capsules disclosed in EP 0 158 449 A1; etherified urea-formaldehyde polymer as disclosed in U.S. Pat. No. 5,204,185; melamine-formaldehyde microcapsules as described in U.S. Pat. No. 4,525,520; cross-linked oil-soluble melamine-formaldehyde precondensate as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-formaldehyde and melamine-formaldehyde Capsules. Urea-formaldehyde and melamine-formaldehyde precondensate microcapsule shell wall precursors are prepared by means of reacting urea or melamine with formaldehyde where the mole ratio of melamine or urea to formaldehyde is in the range of from about 10:1 to about 1:6, preferably from about 1:2 to about 1:5. For purposes of practicing this invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alkanol, e.g., methanol, ethanol, 2-propanol, 3-propanol, 1-butanol, 1-pentanol or 1-hexanol, thereby forming a partial ether where the mole ratio of melamine/urea:formaldehyde:alkanol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. No. 3,516,846, U.S. Pat. No. 6,261,483, and Lee et al. (2002) *J. Microencapsulation* 19:559-569.

Examples of urea-formaldehyde pre-condensates useful in the practice of this invention are URAC 180 and URAC 186, trademarks of Cytec Technology Corp. of Wilmington, Del. Examples of melamine-formaldehyde pre-condensates useful in the practice if this invention, include, but are not limited to, CYMEL U-60, CYMEL U-64 and CYMEL U-65, trademarks of Cytec Technology Corp. of Wilmington, Del. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from about 9:1 to about 1:9, preferably from about 5:1 to about 1:5 and most preferably from about 2:1 to about 1:2.

In one embodiment of the invention, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN series of polyvinyl formamides available from BASF. The molecular weights of these materials can range from 10,000 to 1,000,000.

Urea-formaldehyde or melamine-formaldehyde capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkylmalonates, alkyl aceto acetates and polyvinyl alcohol aceto acetates.

Polyurea Capsules. Polyurea capsules are also well-known in the art. For example, isocyanate-based capsule wall technologies are disclosed in WO 2004/054362; EP, 0 148149; EP 0 017 409 B1; U.S. Pat. Nos. 4,417,916, 4,124,526, 5,583,090, 6,566,306, 6,730,635, WO 90/08468, WO 92/13450, U.S. Pat. Nos. 4,681,806, 4,285,720 and U.S. Pat. No. 6,340,653.

Suitable isocyanates of use in this invention include, for example, 1,5-naphthylene diisocyanate, 4,4'-diphenylmethane diisocyanate (MOI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, and 3,3-bischloromethyl ether 4,4'-diphenyldiisocyanate. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane and dimer fatty acid diisocyanate.

To facilitate wall formation, polyurea capsules can also include cross-linking agents, such as amines or alcohols. Examples of amines of particular use include guanidine amines/salts, amphoteric amines, diamines or a combination thereof.

Water soluble diamines are one class of amines of use in this invention as the amine is usually present in the aqueous phase. One class of such amine is of the type:

where n is ≥1. When n is 1, the amine is a diamine, ethylene diamine. When n is 2, the amine is diamine propane and so on. Exemplary amines of this type include, but are not limited to, ethylenediamine, 1,3-diaminopropane, 1,4-diaminobutane, hexanethylene diamine, hexamethylene diamine, and pentaethylenehexamine. In particular embodiments of this invention, the preferred n is 6, where the amine is a hexamethylene diamine.

Amines that have a functionality greater than 2, but less than 3 and which may provide a degree of cross linking in the shell wall are the polyalykylene polyamines of the type:

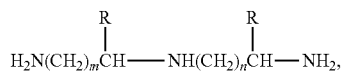

where R equals hydrogen or —CH₃, m is 1-5 and n is 1-5, e.g., diethylene triamine, triethylene tetraamine and the like. Exemplary amines of this type include, but are not limited to diethylenetriamine, bis(3-aminopropyl)amine, bis(hexanethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine, based on this core structure. An example is:

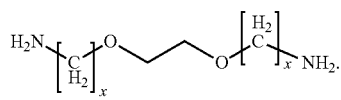

Exemplary polyetheramines include 2,2'-ethylenedioxy)bis (ethylamine) and 4,7,10-trioxa-1,13-tridecanediamine.

Other suitable amines include, but are not limited to, tris(2-aminoethyl)amine, triethylenetetramine, N,N'-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine and 2,4,6-triaminopyrimidine.

Amphoteric amines, i.e., amines that can react as an acid as well as a base, are another class of amines of use in this invention. Examples of amphoteric amines include proteins and amino acids such as gelatin, L-lysine, L-arginine, L-lysine monohydrochloride, arginine monohydrochloride and ornithine monohydrochloride.

Guanidine amines and guanidine salts are yet another class of amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Commercially available examples of amines include JEFFAMINE EDR-148 (where x=2), JEFFAMINE EDR-176 (where x=3) (from Huntsman). Other polyether amines include the JEFFAMINE ED Series, and JEFFAMINE TRIAMINES.

Alcohols of use as cross-linking agents typically have at least two nucleophilic centers. Exemplary alcohols include, but are not limited to, ethylene glycol, hexylene glycol, pentaerythritol, glucose, sorbitol, and 2-aminoethanol.

In another embodiment of the invention, a microcapsule composition is provided that contains an active material that is encapsulated by a polyurea polymer which are reacted in the presence of a capsule formation aid, e.g., a surfactant or dispersant. Classes of protective colloid or emulsifier of use as surfactants or dispersants include maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide, ethylenediamine and ethylene oxide, polyvinylpyrrolidone, polyvinyl alcohols, carboxymethyl cellulose, fatty acid esters of polyoxyethylenated sorbitol and sodium dodecylsulfate.

Commercially available surfactants include, but are not limited to, sulfonated naphthalene-formaldehyde condensates such as MORWET D425 (Akzo Nobel); partially hydrolyzed polyvinyl alcohols such as MOWIOLs, e.g., MOWIOL 3-83 (Air Products); sulfonated polystyrenes such as FLEXAN II (Akzo Nobel).

Typically, hydrocolloids are used to improve the colloidal stability of the slurry against coagulation, sedimentation and creaming. As such, such processing aids can also be used in conjunction with the microcapsules of this invention. As used herein, the term "hydrocolloid" refers to a broad class of water-soluble or water-dispersible polymers having anionic, cationic, zwitterionic or non-ionic character. Hydrocolloids useful for the sake of the present invention include polycarbohydrates, such as starch, modified starch, dextrin, maltodextrin, and cellulose derivatives, and their quaternized forms; natural gums such as alginate esters, carrageenan, xanthanes, agar-agar, pectins, pectic acid, and natural gums such as gum arabic, gum tragacanth and gum karaya, guar gums and quaternized guar gums; gelatin, protein hydrolysates and their quaternized forms; synthetic polymers and copolymers, such as poly(vinyl pyrrolidone-co-vinyl acetate), poly(vinyl alcohol-co-vinyl acetate), poly ((met)acrylic acid), poly(maleic acid), poly(alkyl(meth) acrylate-co-(meth)acrylic acid), poly(acrylic acid-co-maleic acid) copolymer, poly(alkyleneoxide), poly(vinylmethylether), poly(vinylether-co-maleic anhydride), and the like, as well as poly-(ethyleneimine), poly((meth)acrylamide), poly (alkyleneoxide-co-dimethylsiloxane), poly(amino dimethylsiloxane), and the like, and their quartenized forms.

Deposition Aid.

The deposition aid used in accordance with this invention aids in deposition of capsules to surfaces such as fabric, hair or skin. In particular embodiments of this invention, the deposition aid is a terpolymer composed of MAPTAC (methacrylamidopropyl trimethyl ammonium chloride), acrylamide and acrylic acid, with molecular weight (MW) in the range of 100,000 to about 1,200,000, preferably from about 500,000 to about 1,000,000. An exemplary deposition of use in this invention is the ampholytic terpolymer commercially available as MERQUAT 2003PR (Lubrizol Corp., Piscataway, N.J.). These types of terpolymers can also be used in combination with an anionic, nonionic or cationic polymer to provide additional tailoring of performance and product stability. Examples of such polymers include, but are not limited to, polysaccharides (e.g., guar, alginates, starch, xanthan, chitosan, cellulose, dextrans, arabic gum, carrageenan, and hyaluronates), polypeptides (e.g., silk protein, zein, gelatin, keratin, collagen or polylysine), polycarbonates, polyesters, polyolefinic (vinyl, acrylic, acrylamide, poly diene), polyesters, polyethers, polyurethanes, polyoxazolines, polyamines, silicones, polyphosphazines, olyaromatics, poly heterocyclics, or polyionenes Furthermore, the terpolymer can be used as a mixture with a nonionic, cationic, amphoteric or anionic surfactant. Examples of surfactants that can be used in combination with the terpolymer include, but are not limited to, cetyl trimethyl ammonium chloride (CTAC), poloxamers such as PLURONICS (e.g., PLURONIC F127), PLURAFAC (e.g., PLURAFAC F127), or MIRANET-N, saponins such as QNATURALE (National Starch Food Innovation), or a gum Arabic such as Seyal or Senegal.

Any suitable method for coating the deposition aid onto the encapsulated fragrance materials can be used. The nature of suitable polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (covalently) grafted to the capsule or particle surface. Chemical modification of the capsule or particle surface is another way to optimize anchoring of the polymer coating to capsule or particle surface. Furthermore, the capsule and the polymer need to want to go to the desired interface and, therefore, need to be compatible with the chemistry (polarity, for instance) of that interface.

The diameter of the capsules produced in accordance with this invention can vary from about 10 nanometers to about 1000 microns, preferably from about 50 nanometers to about 100 microns and is most preferably from about 2 to about 15 microns. The capsule distribution can be narrow, broad, or multi-modal. Multi-modal distributions may be composed of different types of capsule chemistries.

Active Material. Active materials suitable for use in this invention include without limitation, any combination of fragrance, essential oil, plant extract or mixture thereof that is compatible with, and capable of being encapsulated by, a polymer. Individual perfume ingredients that can be included in the capsules of this invention include fragrances containing:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethylheptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetramethyl-6-octen-3-one, aliphatic sulfur-containing compounds, such as for example 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, α-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8 (5H—)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol;

x) cycloaliphatic alcohols, such as, for example, alpha,3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyldodecahydronaphtho[2,1-b]furan, 3α-ethyl-6,6,9α-trimethyldodecahydronaphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-1-one, 6,7-dihydro-1,1,2,3,3-pentamethyl-4(5H)-indanone, 5-cyclohexadecen-1-one, 8-cyclohexadecen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert-butyl-(2,4-dimethyl-3-cyclohexen-1-yl)ketone;

xv) esters of cyclic alcohols, such as, for example, 2-tert-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, alpha, alpha-dimethylphenylethyl butyrate, cinnamyl acetate, 2-phenoxyethyl isobutyrate, 4-methoxybenzyl acetate, aralphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert-butylphenyl)propanal, 3-(4-tert-butylphenyl) propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methyl-ethyl)-1H-5-indenyl]ethanone, 5',6',7',8'-tetrahydro-3',5',5',6',8',8'-hexamethyl-2-acetonaphthone;

xxi) aromatic and aralphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methy-N-methylanthranilate, Schiff's bases of methyl anthranilate with 7-hydroxy-3,7-dimethyloctanal, 2-methyl-3-(4-tert-butylphenyl)propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin; and xxvi) essential oils, concretes, absolutes, resins, resinoids, balsams, tinctures such as for example ambergris tincture, amyris oil, angelica seed oil, angelica root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, cananga oil, cardamom oil, cascarilla oil, cassia oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oakmoss absolute, elemi oil, estragon oil, eucalyptus citriodora oil, eucalyptus oil (cineole type), fennel oil, fir needle oil, galbanum oil, galbanum resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemon-grass oil, lovage oil, lime oil distilled, lime oil expressed, linaloe oil, Litsea cubeba oil, laurel leaf oil, mace oil, marjoram oil, mandarin oil, massoi (bark) oil, mimosa absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, origanum oil, palmarosa oil, patchouli oil, perilla oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, tagetes oil, fir needle oil, tea tree oil, turpentine oil, thyme oil, Tolu balsam, tonka bean absolute, tuberose absolute, vanilla extract, violet leaf absolute, verbena oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom.

In some embodiments, the amount of encapsulated fragrance oil is from about 80% to about 5% of the total capsule suspension, preferably from about 60% to about 10% of the total capsule suspension, and most preferably from about 50% to about 20% of the total capsule suspension.

In addition to the fragrance materials, the present invention also contemplates the incorporation of other core additives including solvent, emollients, and core modifier materials encapsulated by the encapsulating polymer.

The present invention also contemplates the incorporation of solvent materials, particles or polymeric core modifiers into the core. The solvent materials are hydrophobic materials that are miscible in the fragrance materials used in the present invention. Suitable solvents are those having reasonable affinity for the fragrance chemicals and a Clog P greater than 3.3, preferably greater than 6 and most preferably greater that 10. Suitable materials include, but are not limited to triglyceride oil, mono and diglycerides, mineral oil, silicone oil, diethyl phthalate, polyalpha olefins, castor oil and isopropyl myristate. In a highly preferred embodiment the solvent materials are combined with fragrance materials that have high Clog P values as set forth above. It should be denoted that selecting a solvent and fragrance with high affinity for each other will result in the most pronounced improvement in stability. This specific affinity may be measured by determining the Solvent-Water partition coefficient for the fragrance material. Appropriate solvents include, but are not limited to, mono-, di- and tri-esters, and mixtures thereof, of fatty acids and glycerine. The fatty acid chain can range from C4-C26. Also, the fatty acid chain can have any level of unsaturation. For instance capric/caprylic triglyceride known as NEOBEE M5 (Stepan Corporation). Other suitable examples are the CAPMUL series by Abitec Corporation, for instance CAPMUL MCM. Isopropyl myristate fatty acid esters of polyglycerol oligomers include $R_2CO-[OCH_2-CH(OCOR_1)-CH2O-]_n$, where $R_1$ and $R_2$ can be H or C4-26 aliphatic chains, or mixtures thereof, and n ranges between 2-50, preferably 2-30. Nonionic fatty alcohol alkoxylates like the NEODOL surfactants by BASF, the DOBANOL surfactants by Shell Corporation or the BIOSOFT surfactants by Stepan, wherein the alkoxy group is ethoxy, propoxy, butoxy, or mixtures thereof. In addition, these surfactants can be end-capped with methyl groups in order to increase their hydrophobicity. Di- and tri-fatty acid chain containing nonionic, anionic and cationic surfactants, and mixtures thereof are also contemplated, as are fatty acid esters of polyethylene glycol, polypropylene glycol, and polybutylene glycol, or mixtures thereof. Polyalphaolefins such as the EXXONMOBIL PURESYM PAO line; esters such as the EXXONMOBIL PURESYN esters; mineral oil; silicone oils such polydimethyl siloxane and polydimethylcyclosiloxane; diethyl phthalate; and di-isodecyl adipate can also be included. In certain embodiments, ester oils have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER.

Nanoscale solid particulate materials such as those disclosed in U.S. Pat. No. 7,833,960 may also be incorporated into the core and may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), manganese (Mn), iron (Fe), nickel (Ni), cobalt (Co), copper (Cu), gold (Au), silver (Ag), platinum (Pt) and palladium (Pd).

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a nonlimiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled material include AEROSIL R812, which has a particle size of less than 25 nm according to the specification from the manufacture, Degussa Corp. Other suitable materials from Degussa include, but not limited to, AEROSIL R972, AEROSIL R974, AEROSIL R104, AEROSIL R106, AEROSIL R202, AEROSIL R805, AEROSIL R812, AEROSIL R812S, AEROSIL R816, AEROSIL R7200, AEROSIL R9200, and AEROXIDE $TiO_2$ P25, AEROXIDE T805, AEROXIDE LE1, AEROXIDE LE2, AEROXIDE $TiO_2$ NKT 90, AEROXIDE Alu C805, titanium dioxide PF2, SIPERNAT D110, SIPERNAT D-380. The hydrophobic materials from Deguassa Corp. such as including AEROSILE R812 and R972 are especially preferred.

Nanoscaled materials such as UVINUL $TiO_2$ and Z-COTE HP1 manufactured by BASF can also be used as well as and TI-PURE titanium dioxide, TI-PURE R-700, and TI-SELECT. Additional suitable materials include TS-6200 from Dupont and ZEROFREE 516, HUBERDERM 2000 and HUBERDERM 1000 from the J.M. Huber Corporation, Havre De Grace, MD. Silica products such as SYLOID 63, 244, 72, 63FP 244FP, 72FP, SYLOX 15, 2 and Zeolites such as SYLOSIV A3, SYLOSIV A4 and SYLOSIV K300 from Grace Davison can also be used.

Polymeric core modifiers are also contemplated. It has been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymeric core modifiers include copolymers of ethylene; copolymers of ethylene and vinyl acetate (ELVAX polymers by DOW Corporation); copolymers of ethylene and vinyl alcohol (EVAL polymers by Kuraray); ethylene/acrylic elastomers such as VALNAC polymers by Dupont; polyvinyl polymers, such as polyvinyl acetate; alkyl-substituted cellulose, such as ethyl cellulose (ETHOCEL made by DOW Corporation) and hydroxypropyl celluloses (KLUCEL polymers by Hercules); cellulose acetate butyrate available from Eastman Chemical; polyacrylates (e.g., AMPHOMER, DEMACRYL LT and DERMACRYL 79, made by National Starch and Chemical Company, the AMERHOLD polymers by Amerchol Corporation, and ACUDYNE 258 by ISP Corporation); copolymers of acrylic or methacrylic acid and fatty esters of acrylic or methacrylic acid such as INTELIMER POLYMERS made by Landec Corporation (see also U.S. Pat. Nos. 4,830,855, 5,665,822, 5,783,302, 6,255,367 and 6,492,462); polypropylene oxide; polybutylene oxide of poly(tetrahydrofuran); polyethylene terephthalate; polyurethanes (DYNAM X by National Starch); alkyl esters of poly(methyl vinyl ether); maleic anhydride copolymers, such as the GANTREZ copolymers and OMNIREZ 2000 by ISP Corporation; carboxylic acid esters of polyamines, e.g., ester-terminated polyamides (ETPA) made by Arizona Chemical Company; polyvinyl pyrrolidone (LUVISKOL series of BASF); block copolymers of ethylene oxide, propylene oxide and/or butylenes oxide including, e.g., PLURONIC and SYNPERONIC polymers/dispersants by BASF. Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

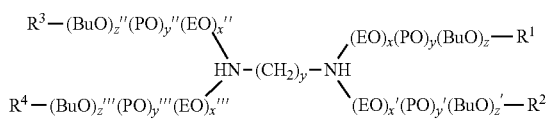

where $R^1$, $R^2$, $R^3$, and $R^4$ are independently H or any alkyl or fatty alkyl chain group. Examples of such polymers are the commercially known as TETRONICS by BASF Corporation.

Sacrificial core ingredients can also be included. These ingredients are designed to be lost during or after manufacture and include, but are not limited to, highly water soluble or volatile materials.

The level of solvent materials, particles or polymeric core modifiers in the core encapsulated by the encapsulating polymer should be greater than about 10 weight percent, preferably greater than about 30 weight percent and most preferably greater than about 70 weight percent. In addition to the solvent, it is preferred that higher Clog P fragrance materials are employed. It is preferred that greater than about 60 weight percent, preferably greater than 80 and more preferably greater than about 90 weight percent of the fragrance chemicals have Clog P values of greater than about 3.3, preferably greater than about 4 and most preferably greater than about 4.5. Those with skill in the art will appreciate that many formulations can be created employing various solvents and fragrance chemicals. The use of a high level of high Clog P fragrance chemicals will likely require a lower level of hydrophobic solvent than fragrance chemicals with lower Clog P to achieve similar performance stability. As those with skill in the art will appreciate, in a highly preferred embodiment, high Clog P fragrance chemicals and hydrophobic solvents comprise greater than about 80, preferably more than about 90 and most preferably greater than 95 weight percent of the fragrance composition. As discussed above, specific Clog P values may be measured between candidate solvents and water for the fragrance materials to be included in the core. In this way, an optimum solvent choice may be made. In fact, since most fragrances will have many ingredients, it may be preferable to measure the partitioning of a specific fragrance blend in solvent and water in order to determine the effect of any material interactions.

Other active materials that can be included the in capsules of this invention include antimicrobial agents such as thymol, 2-hydroxy-4,2,4-trichlorodiphenylether, triclocarban; organic sunscreen actives such as oxybenzone, octylmethoxy cinnamate, butylmethoxy dibenzoyln ethane, p-aminobenzoic acid and octyl dimethyl-p-aminobenzoic acid; vitamins such as Vitamin A, Vitamin C and Vitamin E or esters thereof; and malodor counteracting ingredients including, but not limited to, an $\alpha,\beta$-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, and zinc undecenylate.

As used herein olfactory effective amount is understood to mean the amount of compound in perfume compositions the individual component will contribute to its particular olfactory characteristics, but the olfactory effect of the fragrance composition will be the sum of the effects of each of the fragrance ingredients. Thus, the fragrances of the invention can be used to alter the aroma characteristics of the perfume composition by modifying the olfactory reaction contributed by another ingredient in the composition. The amount will vary depending on many factors including other ingredients, their relative amounts and the effect that is desired.

One object of the present invention is to deposit capsules containing fragrance cores on desired substrates such as cloth, hair, and skin during washing and rinsing processes. Further, it is desired that, once deposited, the capsules release the encapsulated fragrance either by diffusion through the capsule wall, via small cracks or imperfections in the capsule wall caused by drying, physical, or mechanical means, or by large-scale rupture of the capsule wall. In each of these cases, the volatility of the encapsulated perfume materials is critical to both the speed and duration of release, which in turn control consumer perception. Thus, fragrance chemicals which have higher volatility as evidenced by normal boiling points of less than 250° C., preferably less than about 225° C. are preferred in cases where quick release and impact of fragrance is desired. Conversely, fragrance chemicals that have lower volatility (boiling points greater than 225° C.) are preferred when a longer duration of aroma is desired. Of course, fragrance chemicals having varying volatility may be combined in any proportions to achieve the desired speed and duration of perception.

In order to provide the highest fragrance impact from the active material encapsulated capsules deposited on the various substrates referenced above, it is preferred that materials with a high odor-activity be used. Materials with high odor-activity can be detected by sensory receptors at low concentrations in air, thus providing high fragrance perception from low levels of deposited capsules. This property must be balanced with the volatility as described above. Some of the principles mentioned above are disclosed in U.S. Pat. No. 5,112,688.

Further, it is clear that materials other than fragrances may be employed in the system described here. Examples of other materials which may be usefully deposited from rinse-off products using the invention include sunscreens, softening agents, insect repellents, and fabric conditioners, among others.

Applications. The present invention is well-suited for wash-off products. Wash-off products are understood to be those products that are applied for a given period of time and then are removed. These products include personal care, fabric care and cleaning products. Exemplary wash-off fabric care products include laundry detergents, fabric softeners, bleaches, and brighteners. Exemplary wash-off personal care products include shampoos, hair rinses, creams, body washes, bar soaps and the like. Wash-off cleaning products are typically intended for application to a surface for washing/cleaning or for caring/protecting or both. Examples are cleaning products for hard surfaces, e.g., dishes, or textiles. These products may be liquids, solids, pastes, or gels, of any physical form and include surfactant and/or emulsifying systems well-known in the art.

For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, and 4,424,134. Liquid dish detergents are described in U.S. Pat. Nos. 6,069,122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and U.S. Pat. No. 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and U.S. Pat. No. 4,318,818. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681.

Personal care products can be formulated as "water-in-oil" (W/O) type emulsions, "oil-in-water" (O/W) type emulsions or as multiple emulsions, for example of the water-in-oil-in-water (W/O/W) type, as a PIT emulsion, a Pickering emulsion, a micro-emulsion or nano-emulsion. Emulsions that are particularly preferred are of the "oil-in-water" (O/W) type or water-in-oil-in-water (W/O/W) type.

While the preferred coating materials may be simply dissolved in water and mixed with a suspension of capsules prior to addition to the final product, other modes of coating use and application are also possible. These modes include drying the coating solution in combination with the capsule suspension for use in dry products such as detergents, or using higher concentrations of coating such that a gel structure is formed, or combining the coating material with other polymers or adjuvants which serve to improve physical characteristics or base compatibility. Drying or reducing the water content of the capsule suspension prior to coating addition is also possible, and may be preferable when using some coating materials. Further, when using some coating materials it is possible to add the coating to the application base separately from the encapsulated fragrance.

Use of the coating system described herein allows for more efficient deposition of capsules, particles, and dispersed droplets that are coated by the charged polymer. Without wishing to be bound by any theory it is believed that the advantages of the present invention is created by the combination of the charged coating which is helpful in adhering to the substrate to which the product is applied with a capsule or particle containing fragrance. Once the encapsulated particle is adhered to the substrate, the encapsulated fragrance can be delivered by the fracturing or compromising of the polymer coating by actions such as brushing hair, movement of the fabric, brushing of the skin etc.

One measurement of the enhancement of the present invention in delivering the fragrance and other ingredients of the present invention is done by headspace analysis. Headspace analysis can provide a measure of the fragrance material contained on the desired substrate provided by the present invention. The present invention will provide a much higher level of fragrance on the substrate compared to the amount of fragrance deposited on the substrate by conventional means. As demonstrated by the following examples, the present invention can deliver more than about twice the level of fragrance to a substrate than common approaches, preferably more than about three times the level of fragrance and preferably more than about five times the level of fragrance than traditional approaches.

For example, this may be determined by measuring the level of fragrance imparted to a test hair swatch containing fragrance in a shampoo by conventional means as compared to the level of fragrance imparted by the present invention. The same fragrance should be used and similar test hair pieces should be washed in a similar manner. After brushing to release the fragrance from the hair, the level of fragrance on the test hair swatches of the control and the fragrance of the present invention could be measured by headspace analysis. Due to the superior adhesion of fragrance to hair by the present invention, the headspace analysis of the respective samples will demonstrate an improved level of fragrance as compared to fragrance applied by conventional means.

To better control and measure the fragrance release upon brushing or rubbing from a substrate (i.e., hair or cotton cloth), a fixed-weight of the washed and dried substrate is placed in a custom-made glass vessel containing SILCOSTEEL (Resteck Corp., Bellefont, Pa.)-treated steel ball bearings. Headspace is collected from the vessel using a TENAX trap (Supelco, Inc., Ballefonte, Pa.) upon equilibration. A second headspace is collected after the substrate-containing vessel is shaken along with the steel beads on a flat bed shaker for 20 minutes. Fragrance present in the headspace from unshaken and shaken substrates and subsequently absorbed in the TENAX traps is desorbed through a GERSTEL thermal desorption system (Gersteel, Inc., Baltimore, Md.). Desorbed fragrance volatiles are injected into a gas chromatograph (Hewlett-Packard, Model Agilent 6890) equipped with a flame ionization detector. Area counts of individual fragrance components, identified based on the retention time, are then collected and analyzed.

The invention is described in greater detail by the following non-limiting examples.

EXAMPLE 1

Preparation of Cationic Polymer-Coated Capsules

Cationic polymer-coated capsules were prepared by mixing uncoated fragrance-containing capsules with a deposition aid solution. In this example, polyurea capsules or melamine-formaldehyde capsules containing apple fragrance (0.5% NOE) were prepared according to conventional methods. To prepare cationic capsule slurries that contained a cationic deposition aid, MERQUAT 2003PR was mixed with the polyurea capsules or melamine-formaldehyde capsules until homogeneous.

EXAMPLE 2

Preparation of Cationic Capsules-Containing Shampoo for Hair Swatch Washing

Cationic polymer-coated capsules were prepared according to Example 1 and mixed with a model shampoo base (Magick Botanical Shampoo). The resulting shampoo was added to a warm wash liquor containing four virgin hair swatches (approximately 2.5 grams each) and shaken for 2 minutes in a 40° C. water bath. Swatches were taken out of the wash liquor and rinsed sequentially in three glass jars, each containing 600 grams of clean warm water. Washing and rinsing were repeated once and excess water from hair was removed. Hair swatches were line-dried for 24 hours followed by sensory evaluation by a panel of judges. The fragrance intensity was rated on a scale ranging from 0 to 10. A numerical value of 5 indicated the hair swatches produced a strong intensity, while a value of 10 indicated the hair swatches generated a very strong smell.

The results of this analysis indicated that polyurea capsules prepared in accordance with the present invention had a much stronger fragrance intensity compared to polyurea capsules coated with MERQUAT 2001 in the pre- and post-rubbing stage and were able to deliver the full benefit of the fragrance formulation. See FIG. 1.

Figure 2:
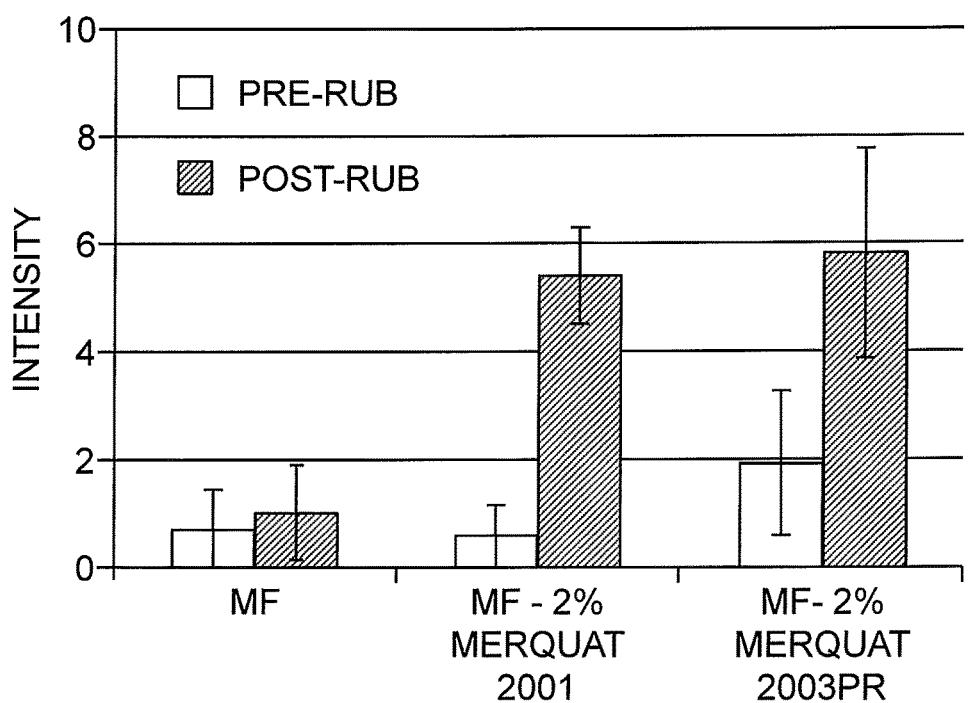
FIG. 2 shows sensory performance of melamine-formaldehyde (MF) capsules of the invention in a hair shampoo formulation. Data are the averages from two separate experiments.

Similarly, melamine-formaldehyde capsules prepared in accordance with the present invention had a much stronger fragrance intensity compared to melamine-formaldehyde capsules or melamine-formaldehyde capsules coated with MERQUAT 2001 in the pre- and post-rubbing stage and were able to deliver the full benefit of the fragrance formulation. See FIG. 2.

EXAMPLE 3

Body Wash

An exemplary body wash is composed of PLANTAPON 611 L (SLES, Cap Betaine, Lauryl Glycoside; 22%), ammonium lauryl sulfate (2.5%), LAMESOFT OP65 (Coco Glucoside, Glyceryl Oleate; 3%), POLYQUATERNIUM 10-10 (0.5%), acrylates copolymer (0.5%), neat fragrance (0.3%), cationic polymer coated encapsulated fragrance (1%), DMDM hydantoin (0.3%), glycerin (3%) and water (q.s. 100%).

EXAMPLE 4

Hair Products

An exemplary 2-in-1 hair shampoo is composed of sodium laureth sulfate (10%), cocamidopropyl betaine (7%), glyceryl stearate (2%), cetearyl alcohol (3%), panthenol (0.2%), acrylates copolymer (1.2%), dimethicone (1.5%), POLYQUATERNIUM 10 (0.2%), cationic polymer coated encapsulated fragrance (1%), preservative (as needed), water (q.s. 100%), and NaOH to pH 6.0.

What is claimed is:

1. A personal or fabric care composition comprising an active material, said active material encapsulated by a polyurea microcapsule to provide a polymer encapsulated active material, the polyurea encapsulated active material is further coated by a terpolymer comprising methacrylamidopropyl trimethyl ammonium chloride, acrylamide and acrylic acid.

2. The personal or fabric care product of claim 1, wherein said product is a hair shampoo, hair rinse, bar soap, or body wash.

3. The composition of claim 1, wherein the terpolymer is combined with an anionic, nonionic or cationic polymer to provide additional tailoring of performance and product stability.

4. The composition of claim 1, wherein the terpolymer is combined with a nonionic, cationic, amphoteric or nonionic surfactant.

5. A method of using the composition of claim 1 for imparting an olfactory effective amount of fragrance into a wash-off product comprising
   (a) encapsulating a fragrance material with a polyurea to form a polymer encapsulated fragrance;
   (b) providing a terpolymer comprising methacrylamidopropyl trimethyl ammonium chloride, acrylamide and acrylic acid to the surface of the polyurea encapsulated fragrance to form the composition of claim 1 that contains a coated polyurea encapsulated fragrance; and
   (c) providing the composition of claim 1 to a wash-off product.

6. The composition of claim 1, wherein the active material is a fragrance.

7. The composition of claim 1, wherein the terpolymer has a molecular weight of 100,000 to 1,200,000.

8. The composition of claim 7, wherein the terpolymer has a molecular weight of 500,000 to 1,000,000.

9. The personal or fabric care product of claim 2, wherein said product is a hair shampoo.

\* \* \* \* \*